US 8,246,551 B2

(12) United States Patent
Miller et al.

(10) Patent No.: US 8,246,551 B2
(45) Date of Patent: Aug. 21, 2012

(54) ADAPTER ASSEMBLY FOR STEREOTACTIC BIOPSY

(75) Inventors: Michael E. Miller, Trafalgar, IN (US); Joseph L. Mark, Indianapolis, IN (US); Ronald L. Hofmann, Brazil, IN (US); Terry D. Hardin, Irvine, CA (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 331 days.

(21) Appl. No.: 12/624,194

(22) Filed: Nov. 23, 2009

(65) Prior Publication Data
US 2010/0069787 A1    Mar. 18, 2010

Related U.S. Application Data

(62) Division of application No. 10/803,698, filed on Mar. 18, 2004, now Pat. No. 7,628,762.

(60) Provisional application No. 60/455,992, filed on Mar. 19, 2003.

(51) Int. Cl.
*A61B 10/00* (2006.01)
(52) U.S. Cl. ........................................ 600/564; 606/130
(58) Field of Classification Search .......... 600/562–568; 606/167, 170; 604/19, 22, 27
See application file for complete search history.

(56) References Cited

U.S. PATENT DOCUMENTS

| | | |
|---|---|---|
| 5,871,448 A | 2/1999 | Ellard |
| 5,871,487 A | 2/1999 | Warner et al. |
| 5,902,310 A | 5/1999 | Foerster et al. |
| 6,007,497 A | 12/1999 | Huitema |
| 6,120,463 A | 9/2000 | Bauer |
| 6,193,673 B1 | 2/2001 | Viola et al. |
| 6,451,027 B1 | 9/2002 | Cooper et al. |
| 6,551,253 B2 | 4/2003 | Worm et al. |
| 6,554,779 B2 | 4/2003 | Viola et al. |
| 6,638,235 B2 | 10/2003 | Miller et al. |
| 6,659,956 B2 | 12/2003 | Barzell et al. |
| 7,166,114 B2 | 1/2007 | Moctezuma De La Barrera et al. |
| 2001/0039378 A1 | 11/2001 | Lampman et al. |
| 2002/0120211 A1 | 8/2002 | Wardle et al. |
| 2004/0077972 A1 | 4/2004 | Tsonton et al. |

FOREIGN PATENT DOCUMENTS

DE                935625 C      11/1955

OTHER PUBLICATIONS

PCT International Search Report #PCT/US2004/008380 dated Mar. 19, 2004.

*Primary Examiner* — Max Hindenburg
*Assistant Examiner* — Jonathan M Foreman
(74) *Attorney, Agent, or Firm* — Vista IP Law Group LLP

(57) ABSTRACT

An adapter is provided for use with a biopsy device that includes a cutting element having an outer cannula hub removably mounted to a handpiece. The cutting element includes an outer cannula connected to the outer cannula hub and an inner cannula disposed within the outer cannula and attached to the handpiece. The outer cannula hub allows removal of the handpiece and inner cannula from the outer cannula. The adapter includes a base, a cradle moveably mounted to the base and configured to rotatably support the biopsy device therein, and an indexing guide moveable with the cradle having a receptacle within which the outer cannula hub is rotatably received. The cradle and indexing guide are configured to inhibit rotation and axial movement of the biopsy device relative to the cradle, and facilitates removal of the handpiece and inner cannula from the outer cannula, while maintaining registration with the biopsy site.

19 Claims, 9 Drawing Sheets

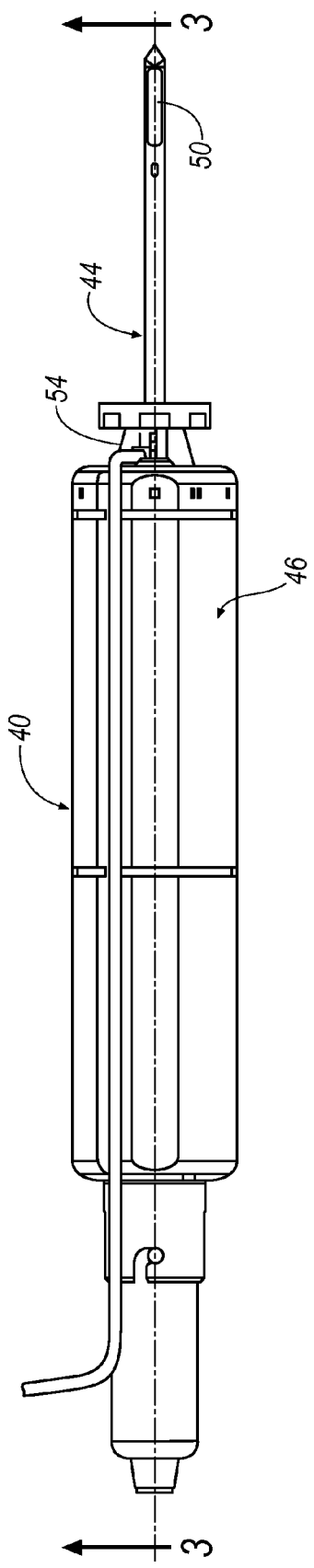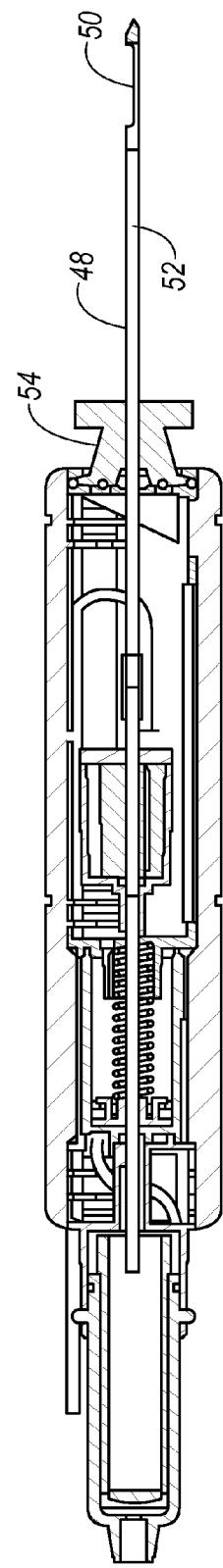
FIG. 2
FIG. 3

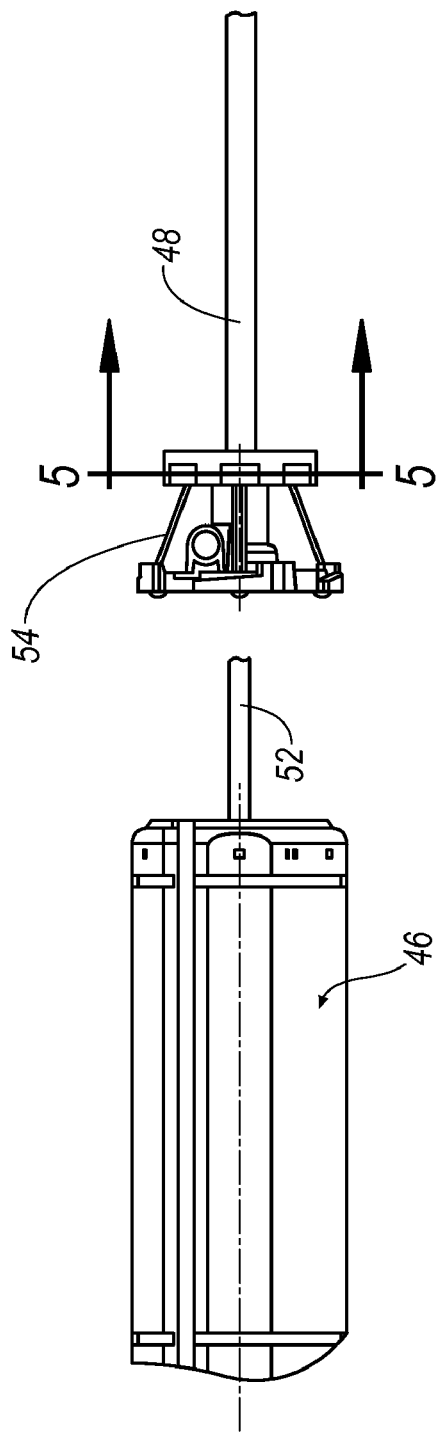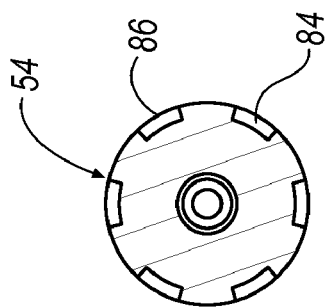
FIG. 4
FIG. 5

ADAPTER ASSEMBLY FOR STEREOTACTIC BIOPSY

CROSS REFERENCE TO RELATED APPLICATIONS

This application is a Divisional application of U.S. Ser. No. 10/803,698 filed on Mar. 18, 2004, which application claims priority to U.S. Provisional Application 60/455,922 filed on Mar. 19, 2003, which applications are incorporated herein by reference in their entirety.

BACKGROUND OF THE INVENTION

1. Field of the Invention

The present invention relates generally to stereotactic breast biopsy systems and more particularly to an adapter assembly suitable for use in a stereotactic breast biopsy system to support a biopsy device.

2. Description of the Related Art

Stereotactic breast biopsy systems are a precise, minimally invasive diagnostic tool for use in performing fine-needle aspiration and needle core biopsies of the human breast to determine whether a breast lesion is benign or malignant. Needle biopsies, unlike more invasive surgical procedures, are typically performed on an out-patient basis with local anesthesia. Stereotactic breast biopsy systems generally include an ergonomically contoured table that comfortably supports the patient in a stable, fixed position that exposes the patient's breast. Stereotactic breast biopsy systems also generally include a diagnostic imaging system for targeting the lesion to be biopsied. The location of the target lesion is used by a guidance system to guide insertion of the biopsy needle into the patient's breast tissue.

The biopsy needle used in a stereotactic breast biopsy is typically a component of a biopsy device, which is supported by the guidance system in an appropriate adapter. Recently there has been developed an improved biopsy device that includes a cutting element mounted to a handpiece. The cutting element includes an outer cannula defining a tissue receiving opening and an inner cannula concentrically disposed within the outer cannula and connected to the handpiece. An outer cannula hub is removably mounted to the handpiece and is connected to the outer cannula. The outer cannula hub allows removal of the handpiece and inner cannula from the outer cannula, leaving the outer cannula in position within the patient's breast tissue to serve as an introducer for biopsy site markers and therapeutics.

During a biopsy procedure it is desirable that the cutting element be accurately positioned adjacent the lesion and remain there throughout the procedure. While conventional adapters selectively inhibit rotation of the biopsy device, once the device is removed, they do not maintain registration with the biopsy site along the Z-axis, i.e., the axis that extends into and out of the patient's body. It is also desirable that the outer cannula, particularly the tissue receiving opening, remain in registration with the biopsy site after removal of the handpiece and inner cannula. Conventional adapters are unequipped to handle removal of the handpiece and inner cannula from the outer cannula, let alone maintain consistent registration between the outer cannula and the biopsy site after removal of the handpiece and inner cannula.

Accordingly, an improved stereotactic adapter is required that facilitates removal of the handpiece and inner cannula, while leaving the outer cannula in position to serve as an introducer for biopsy site markers and therapeutics. An improved stereotactic adapter is also required that maintains consistent registration of the outer cannula with the biopsy site throughout a biopsy procedure, even after removal of the handpiece and inner cannula.

SUMMARY OF THE INVENTION

An adapter assembly is provided for use with a biopsy device that includes a cutting element and an outer cannula hub removably mounted to a handpiece. The cutting element includes an outer cannula connected to the outer cannula hub and an inner cannula disposed within the outer cannula and attached to the handpiece. The outer cannula hub allows removal of the handpiece and inner cannula from the outer cannula. The adapter includes a base, a cradle moveably mounted to the base and configured to rotatably support the biopsy device therein, and an indexing guide movable with the cradle that includes a receptacle within which the outer cannula hub is rotatably received. The cradle and indexing guide are configured to inhibit rotation and axial movement of the biopsy device relative to the cradle, and facilitate removal of the handpiece and inner cannula from the outer cannula, while maintaining registration with the biopsy site.

Among other features, the adapter of the present invention provides the ability to lock the biopsy device into the adapter to inhibit movement therebetween and maintains registration with the biopsy site throughout the biopsy procedure. The adapter of the present invention facilitates the removal of the handpiece and inner cannula, while leaving the outer cannula in position within a patient to serve as an introducer for biopsy site markers, therapeutics or the like. The prevent invention maintains consistent registration of the outer cannula with the biopsy site, even after the handpiece and inner cannula are removed from the outer cannula. The adapter of the present invention also allows the handpiece, outer cannula hub and outer cannula to be removed during a biopsy procedure and replaced with a separate medical instrument, such as an applicator device that allows the insertion of a site maker, therapeutics or the like.

BRIEF DESCRIPTION OF THE DRAWINGS

The features and inventive aspects of the present invention will become more apparent upon reading the following detailed description, claims, and drawings, of which the following is a brief description:

FIGS. 2-4 are various illustrations of a biopsy device for use with the adapter of the present invention;

FIG. 5 is a cross-sectional view of a cannula hub for use with the adapter of the present invention;

DETAILED DESCRIPTION

Figure 1:
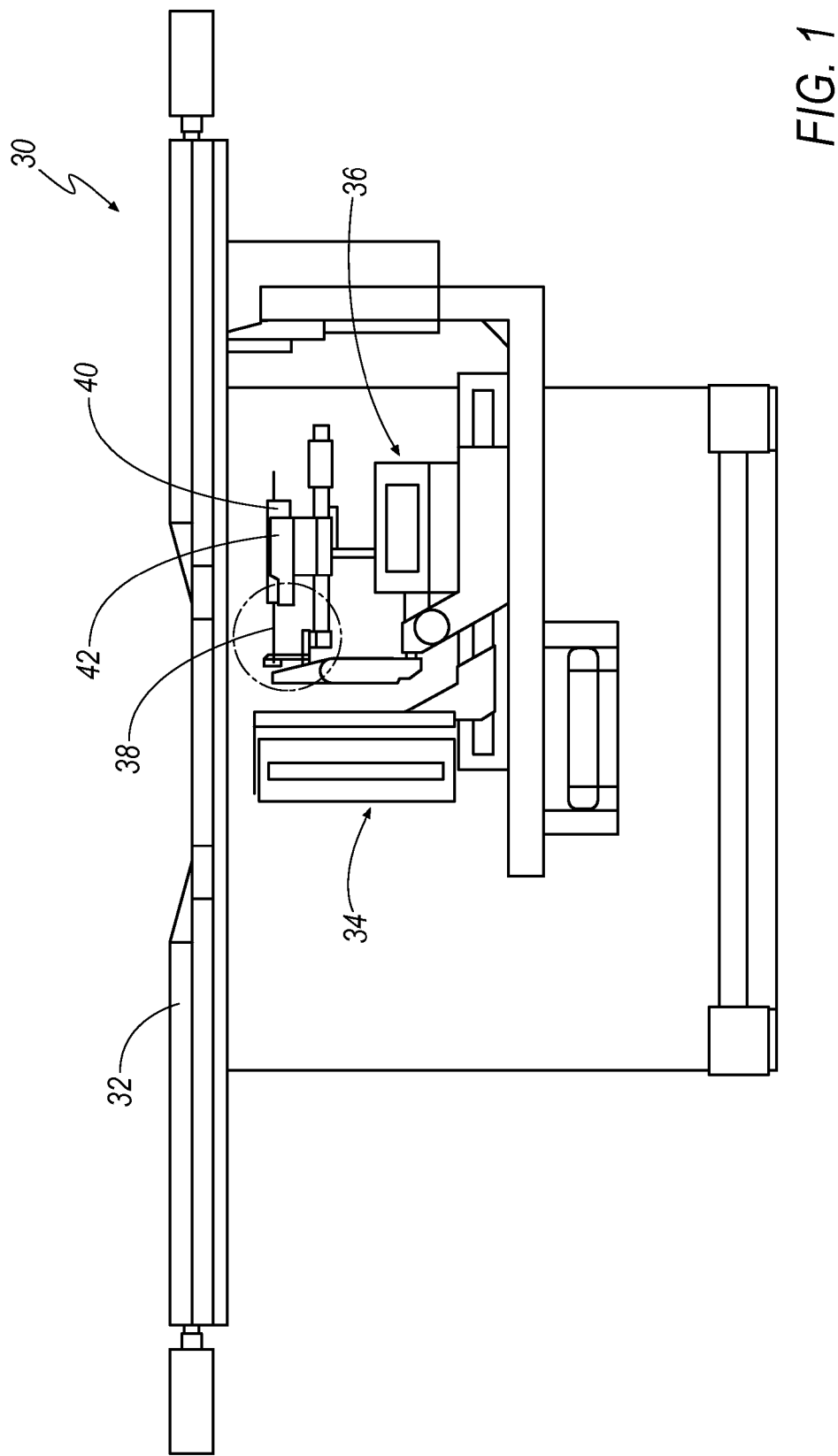
FIG. 1 is a simplified elevational view of an exemplary stereotactic biopsy system.
Figure 6:
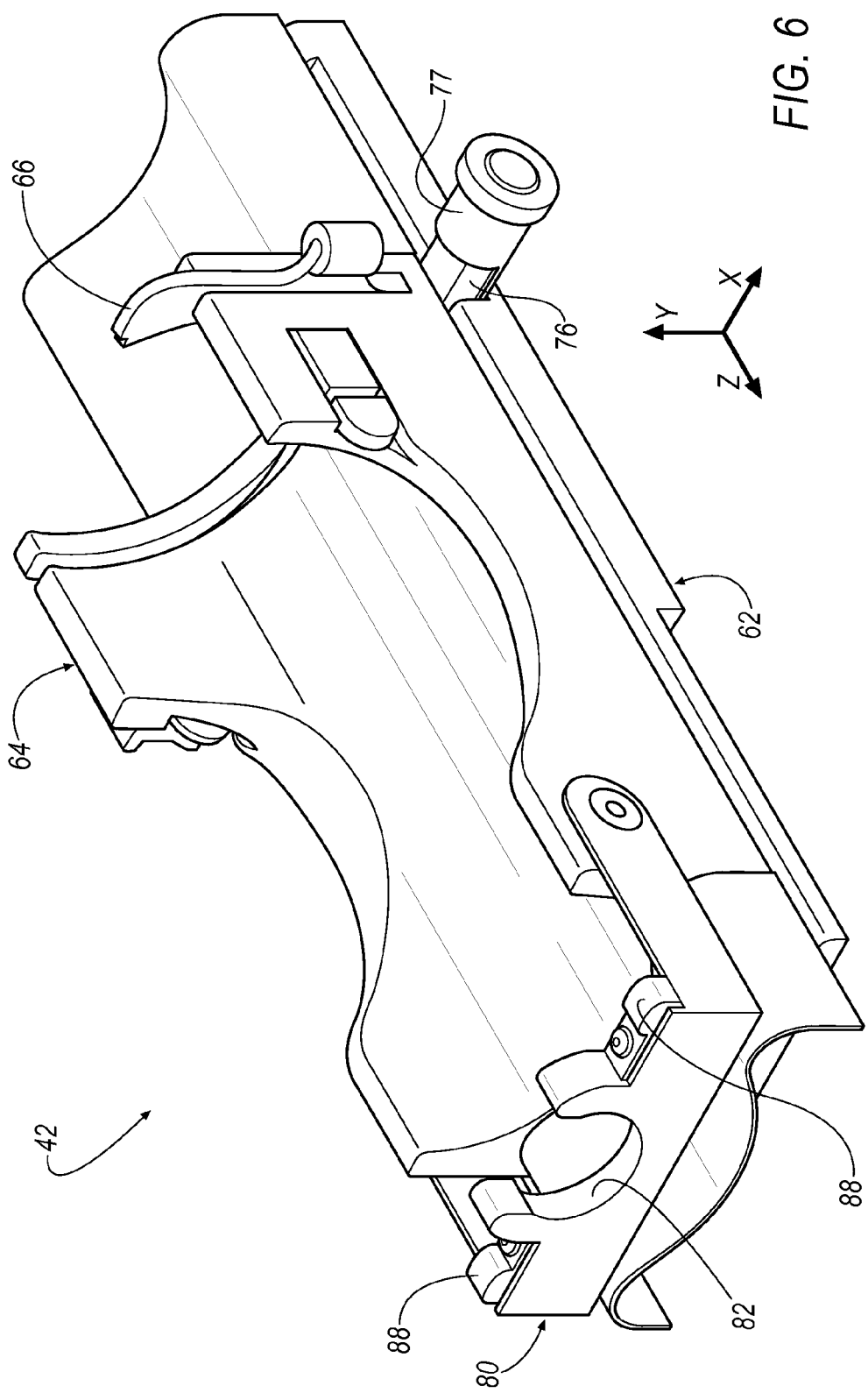
FIG. 6 is a perspective view of an adapter assembly according to an embodiment of the present invention.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Referring to FIG. 1, there is shown a simplified illustration of an exemplary stereotactic breast biopsy system 30 for use in performing fine-needle aspiration and needle core biopsies of the human breast to determine whether a breast lesion is benign or malignant. Stereotactic breast biopsy system 30 includes an ergonomically contoured table 32 that comfortably supports the patient (not shown) in a stable, fixed position that exposes the patient's breast. Stereotactic breast biopsy system 30 also includes a diagnostic imaging system 34 for targeting the lesion to be biopsied. The location of the target lesion is used by a guidance system 36 to guide insertion of a biopsy needle 38 into the patient.

In the disclosed embodiment, the biopsy needle 38 is a component of a biopsy device 40 that is supported by guidance system 36 in an adapter 42. An exemplary biopsy device for use in stereotactic breast biopsy system 30 is the biopsy device marketed by the assignee of the present invention, Suros Surgical Systems, Inc. of Indianapolis, Ind., under the name ATEC™ (Automated Tissue Excision and Collection) and disclosed in U.S. patent application Ser. Nos. 09/707,022 and U.S. Pat. No. 6,638,235, which are also owned by the assignee of the present invention and hereby incorporated by reference in their entity.

Referring to FIGS. 2-5, biopsy device 40 includes a biopsy needle or cutting element 44 mounted to a handpiece 46. The cutting element 44 includes an outer cannula 48 defining a tissue receiving opening 50 and an inner cannula 52 concentrically disposed within the outer cannula 48. An outer cannula hub 54 is removably mounted to the handpiece 46 and is connected to the outer cannula 48. As shown in FIG. 4, outer cannula hub 54 allows removal of handpiece 46 and inner cannula 52 from outer cannula 48, leaving outer cannula 48 positioned within the breast tissue to serve as an introducer for biopsy site markers, therapeutics or the like.

Figure 7:
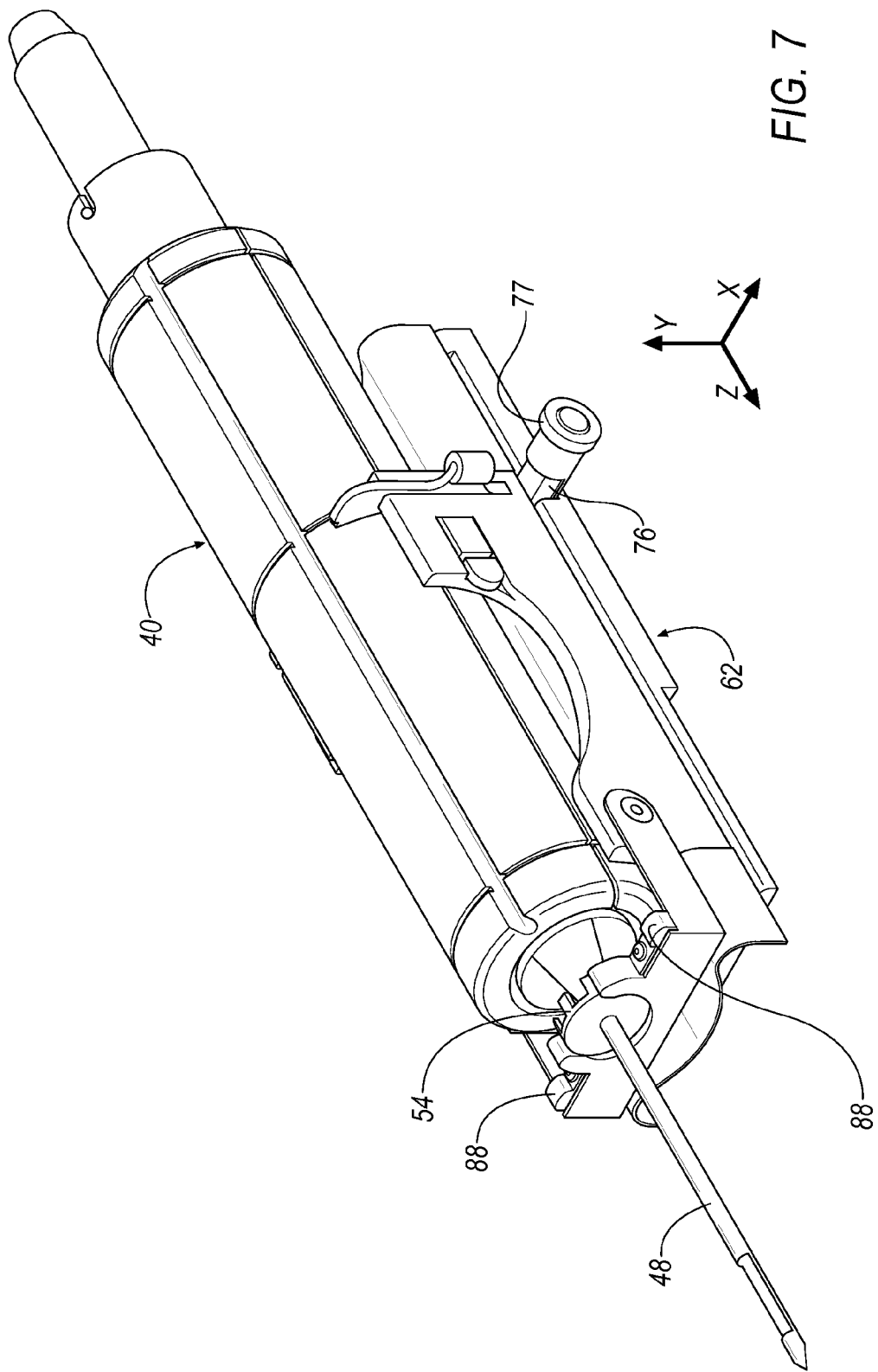
FIG. 7 is a perspective view of the adapter assembly of FIG. 6, illustrating the biopsy device of FIGS. 2-4 being supported by the adapter.
Figure 9:
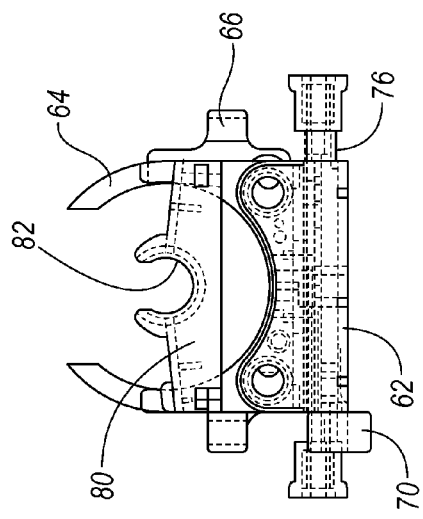
FIG. 9 is a front elevation view of the adapter assembly of FIG. 8.
Figure 10:
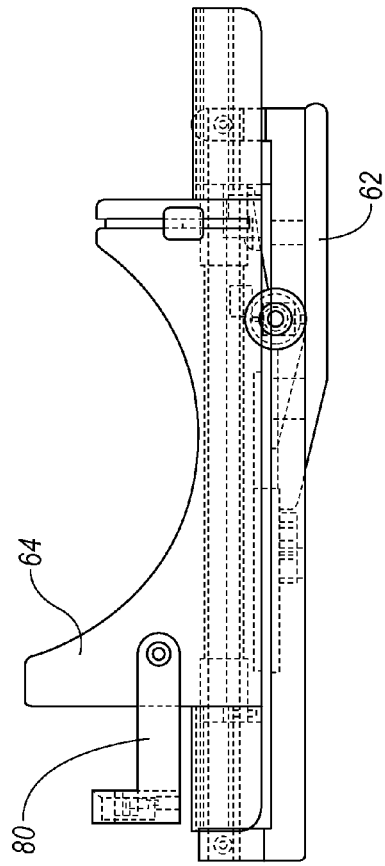
FIG. 10 is a side elevation view of the adapter assembly of FIG. 8.
Figure 8:
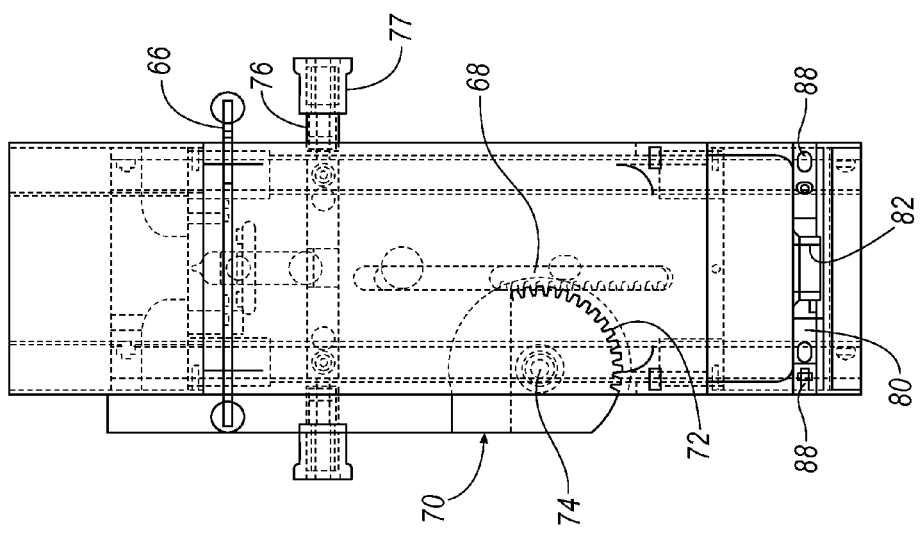
FIG. 8 is a top view of an adapter assembly according to an embodiment of the present invention.

Referring now to FIGS. 6-16, an adapter assembly 42 according to an embodiment of the present invention is shown for use in stereotactic biopsy system 30 to support biopsy device 40. Adapter 42 includes a base 62 upon which a handpiece cradle 64 is moveably secured. Base 62 is attached to guidance system 36 and handpiece cradle 64 receives handpiece 46 of biopsy device 40, as shown in FIG. 7. Handpiece 46 is rotatable within handpiece cradle 64 and can be locked in any one of several angular positions within handpiece cradle 64 by a pivotable clamp 66. Clamp 66 is attached to handpiece cradle 64 and is pivotable between an unlocked position, wherein the handpiece 46 is free to rotate within handpiece cradle 64, and a locked position shown in FIGS. 6 and 7, wherein clamp 66 engages an outer surface of handpiece 46 to inhibit rotation. Additionally, clamp 66 cooperates with handpiece cradle 64 to inhibit axial movement of handpiece 46, i.e., movement along axis Z in FIG. 6, when clamp 66 is pivoted to the locked position.

Handpiece cradle 64 is moveable between a pre-deployment position, in which cutting element 44 is removed from the patient's breast tissue, and a post deployment position, in which cutting element 44 is inserted in the patient's breast tissue. A deployment mechanism is provided between handpiece cradle 64 and base 62, which is operable to rapidly move handpiece cradle 64 and biopsy device 40 relative to base 62 along the Z-axis. In a particular configuration shown FIGS. 8-10, the deployment mechanism includes a gear rack 68 attached to handpiece cradle 64 and a lever 70 moveably attached to base 62. Lever 70, which includes a geared cam end 72 intermeshed with gear rack 68, is rotatable about a pivot point 74 to move gear rack 68 and handpiece cradle 64 between a deployed position and a cocked position ready for deployment. The deployment mechanism also includes a release member 76 that is engagable with handpiece cradle 64 in the cocked position and selectively disengagable therefrom to release handpiece cradle 64 for movement toward the deployed position.

In the illustrated embodiment, the deployment mechanism includes at least one spring that provides the force necessary to move handpiece cradle 64 toward the deployed position. The spring is energized when handpiece cradle 64 is moved to the cocked position and forces handpiece cradle 64 toward the deployed position when release member 76 is disengaged from handpiece cradle 64. In an embodiment, the spring is a torsion or coil spring that is disposed between base 62 and lever 70. As lever 70 is rotated about pivot point 74 to move handpiece cradle 64 to the cocked position, the coil spring is energized. When handpiece cradle 64 is released for movement toward the deployed position, the coil spring forces rotation of lever 70 and a corresponding movement of handpiece cradle 64 via gear rack 68.

The deployment mechanism may also includes a safety 77 that is operably connected to release member 76. The safety 77 prevents accidental disengagement of release member 76 from handpiece cradle 64, but is manipulable to selectively permit disengagement of release member 76 from handpiece cradle 64 when so desired. The above-described deployment mechanism configuration is provided for example only and is not intended to limit the scope of the present invention.

Adapter 42 also includes an indexing or "cannula" guide 80 that is secured for movement with handpiece cradle 64. In an embodiment, indexing guide 80 includes a generally circular-shaped receptacle 82 within which a portion of outer cannula hub 54 is received. Outer cannula hub 54 is rotatable within receptacle 82 or may be locked in any one of several angular positions. Additionally, indexing guide 80 inhibits axial movement (i.e., movement along the Z-axis) of outer cannula hub 54 relative to handpiece cradle 64 and indexing guide 80.

As shown in FIG. 5, a portion of outer cannula hub 54 includes at least one notch 84 in an outer circumferential surface 86 thereof. To lock outer cannula hub 54 against rotation within receptacle 82, indexing guide 80 includes at least one guide lock 88 that is moveably attached to indexing guide 80. When received in receptacle 82, outer cannula hub 54 is rotatable within receptacle 82 to align notch 84 with guide lock 88. Guide lock 88 is moveable generally perpendicular to the Z-axis between an unlocked position (see FIGS.

13 and 16), wherein guide lock 88 is disengaged with outer cannula hub 54, and a locked position (see FIGS. 14 and 15), wherein guide lock 88 is received within notch 84. Once guide lock 88 is moved into notch 84, outer cannula hub 54 can neither rotate nor move axially with respect to indexing guide 80 and handpiece cradle 64. To provide multiple angular positions for tissue receiving opening 50, outer cannula hub 54 may include a plurality of notches 84, as shown in the drawings.

Referring to FIGS. 11-16, an embodiment of indexing guide 80 will be described in greater detail. In the illustrated embodiment, indexing guide 80 is generally U-shaped when viewed from above (see FIG. 11) having a pair of legs 90, which are attachable to cradle 64, and a base 92 within which receptacle 82 is positioned. Base 92 includes a pair of slightly tapered channels 94 within which a guide lock 88 is movably received. In the illustrated embodiment, each guide lock 88 is movably secured within channel 94 by a fastener 96, such as a screw or the like. To facilitate movement of guide locks 88 within channels 94, guide locks 88 may include an elongated slot 98 within which fastener 96 is disposed. Guide locks 88 may optionally include one or more dimples 100 that extend from a lower surface thereof and are received in a hole 102 in base 92 to resist accidental movement of guide locks 88 between the locked and unlocked positions.

Figure 11:
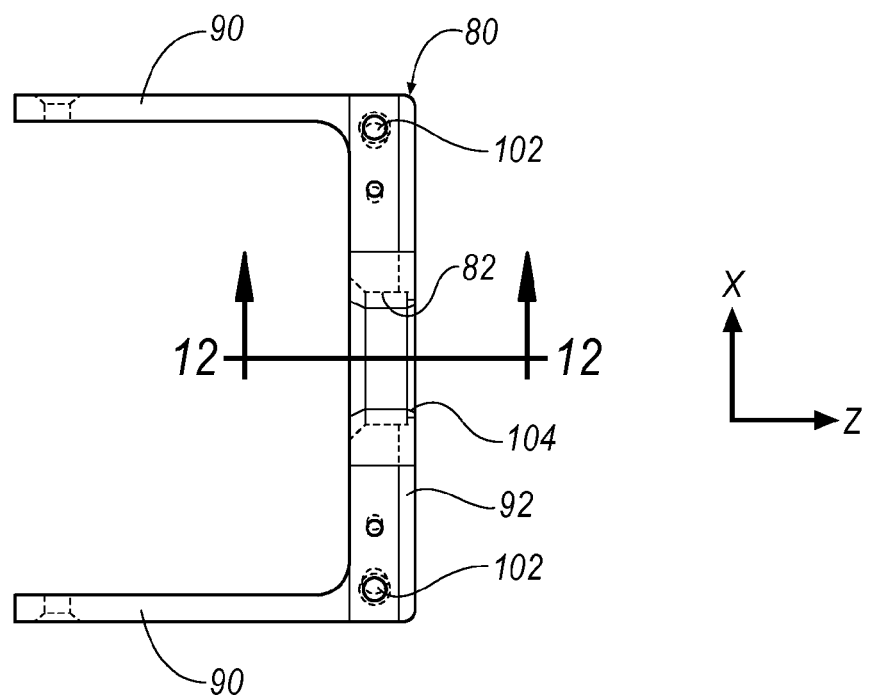
FIG. 11 is a top view of an indexing guide according to an embodiment of the present invention.
Figure 12:
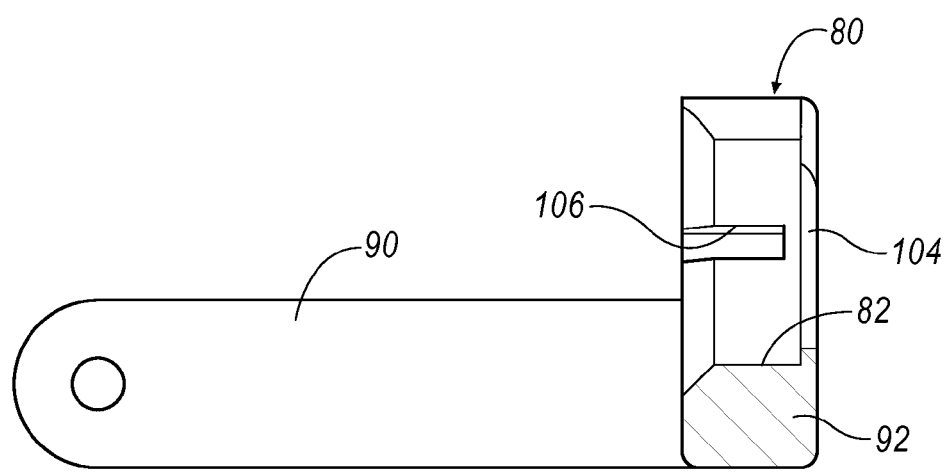
FIG. 12 is a cross-sectional view of the indexing guide of FIG. 11 taken along lines 12-12.
Figure 13:
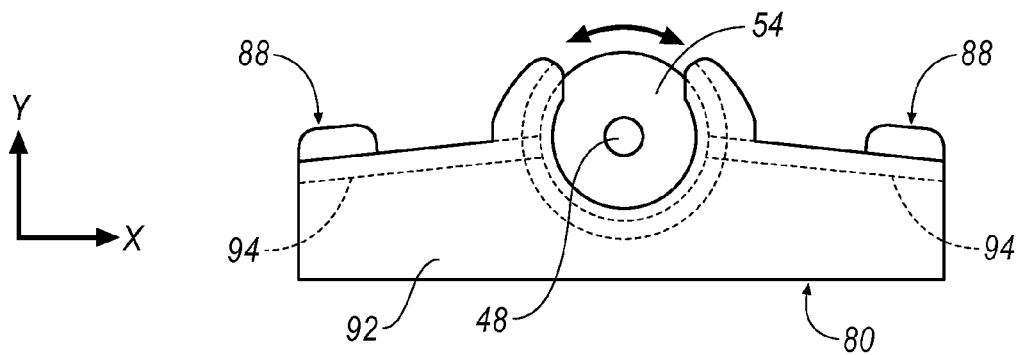
FIG. 13 is a front elevation view of the indexing guide and cannula hub, wherein the cannula hub is unlocked from the indexing guide and free to rotate.
Figure 14:
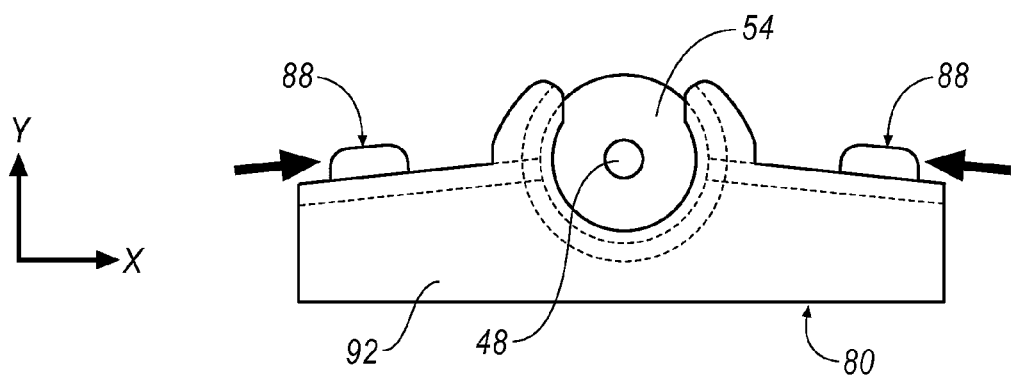
FIG. 14 is a front elevation view of the indexing guide and cannula hub, wherein the cannula hub is locked to the indexing guide and prevented from rotating.

Referring specifically to FIGS. 11 and 12, base 92 may include a lip 104 adjacent receptacle 82 having an inner diameter slightly smaller than the inner diameter of receptacle 82. Cannula hub 54 engages lip 104 when received within receptacle 82 to prevent movement of cannula hub 54 in a first direction along the Z-axis. Base 92 may also include a pair of grooves 106 that extend from channels 94 into receptacle 82 to permit movement of at least a portion of guide locks 88 into receptacle 82.

Figure 15:
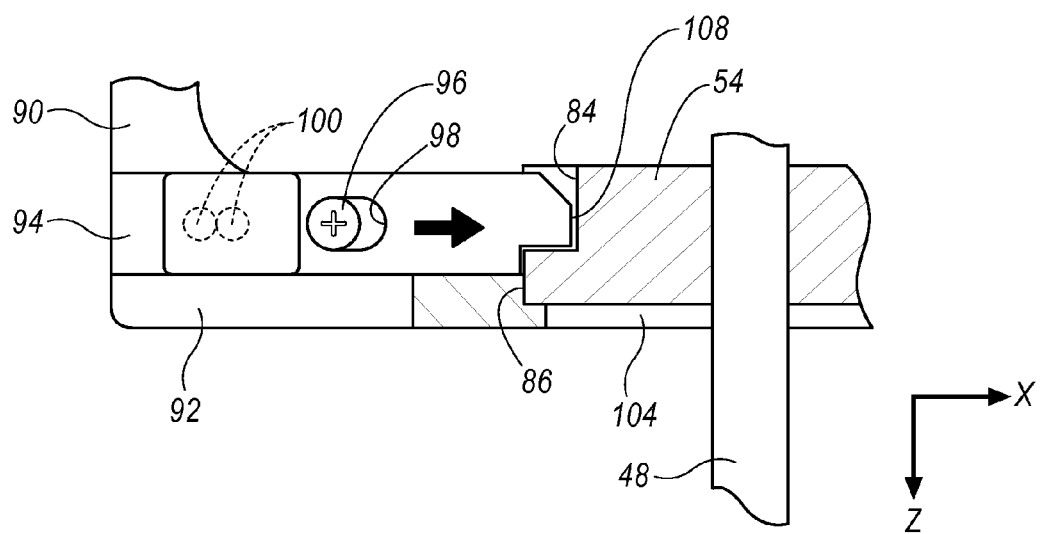
FIG. 15 is a detailed partial cross-sectional view of the indexing guide and cannula hub, wherein the cannula hub is locked to the indexing guide.
Figure 16:
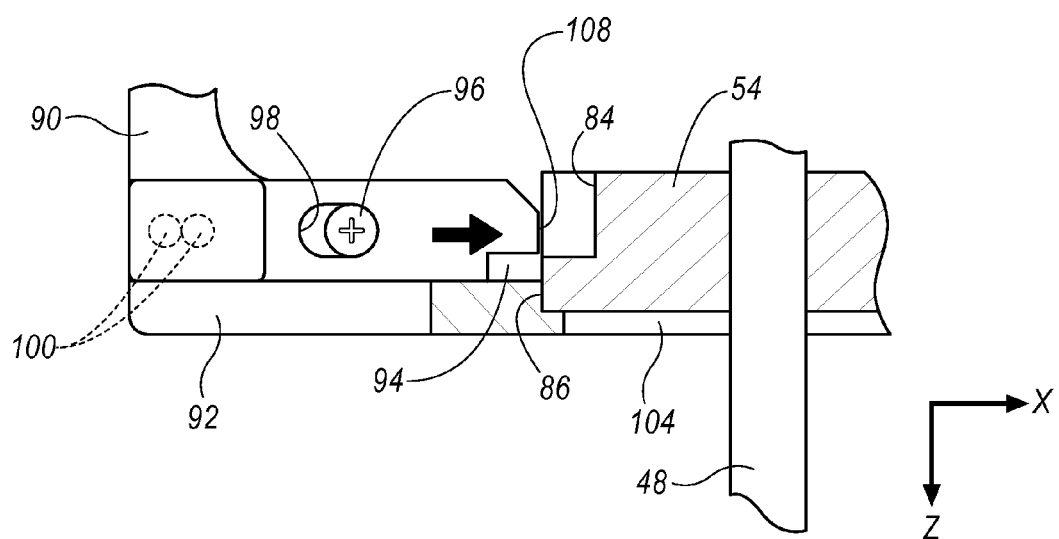
FIG. 16 is a detailed partial cross-sectional view of the indexing guide and cannula hub, wherein the cannula hub is unlocked from the indexing guide.

As shown in FIGS. 15 and 16, guide locks 88 include an engagement end 108 configured for receipt into notches 84 on cannula hub 54. When guide locks 88 are moved into the locked position shown in FIG. 15, engagement end 108 is received in a notch 84 to inhibit both rotation and axial movement of cannula hub 54 in a second direction along the Z-axis opposite the first direction inhibited by lip 104. However, when guide locks 88 are moved to the unlocked position shown in FIG. 16, cannula hub 54 is free to rotate within receptacle 82.

The adapter 42 of the present invention provides the ability to lock biopsy device 40 into the adapter 42 to inhibit movement therebetween, and maintains registration with the biopsy site throughout a biopsy procedure. The adapter 42 facilitates the removal of handpiece 46 and inner cannula 52 from outer cannula 48 by unlocking clamp 66 from handpiece 46 and leaving guide locks 88 engaged with outer cannula hub 54. This feature allows the outer cannula 48 to remain in position within the patient's breast tissue to serve as an introducer for biopsy site markers and therapeutics. By locking outer cannula hub 54 with cannula guide 80, adapter 42 maintains consistent registration of the outer cannula 48 with the biopsy site, even after the handpiece 46 and inner cannula 52 are removed from the outer cannula 48.

The adapter of the present invention also allows the handpiece 46, inner cannula 52, outer cannula hub 54 and outer cannula 48 to be removed from the adapter 42 during a biopsy procedure and replaced with a separate medical instrument (not shown), such as an applicator device that allows the insertion of a site maker and therapeutics. The separate applicator device may include a cannula hub substantially similar to outer cannula hub 54 found in biopsy device 40. However, unlike the outer cannula 48 found in the biopsy device, the outer cannula in the applicator device includes an open end, instead of an end having a trocar tip and a tissue receiving opening 50.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A biopsy system, comprising:
   a biopsy device supported by an adapter, wherein the biopsy device comprises a handpiece and a cutting element having an outer cannula hub removably mounted to the handpiece, wherein the cutting element comprises an outer cannula and an inner cannula disposed within the outer cannula and attached to the handpiece, wherein the outer cannula is connected to the outer cannula hub and defines a tissue receiving opening on a circumferential portion of the outer cannula, wherein the outer cannula hub allows selective removal of the handpiece and inner cannula from the outer cannula; and
   wherein the adapter comprises:
   a base;
   a cradle moveably mounted to the base such that the cradle may move while attached to the base, and wherein the cradle is configured to rotatably support the handpiece therein, the cradle configured to inhibit axial movement of the handpiece relative to the cradle when locked therein; and
   an indexing guide moveable with the cradle and including a receptacle within which the outer cannula hub is rotatably received, the indexing guide configured to inhibit rotation and axial movement of the outer cannula hub and outer cannula relative to the indexing guide and the cradle when the outer cannula hub is locked therein.

2. The system of claim 1, wherein the indexing guide includes at least one guide lock that is selectively engagable with the outer cannula hub to inhibit rotation and axial movement thereof.

3. The system of claim 2, wherein the indexing guide includes two guide locks.

4. The system of claim 2, wherein the guide lock is moveably secured to the indexing guide.

5. The system of claim 2, wherein the outer cannula hub includes at least one notch and the guide lock is configured to be received in the notch to prevent movement of the outer cannula hub in a first axial direction.

6. The system of claim 1, wherein the indexing guide includes a lip configured to prevent movement of the outer cannula hub in a second axial direction.

7. The system of claim 1, wherein the cradle includes a clamp member that is selectively engagable with a portion of the handpiece to inhibit movement of the handpiece relative to the cradle.

8. The system of claim 1, wherein the adapter includes a deployment mechanism configured to move the cradle relative to the base.

9. The system of claim 8, further comprising a gear rack attached to the cradle and a lever movably attached to the base, wherein the lever includes a geared cam end intermeshed with the gear rack.

10. The system of claim 9, wherein a biasing member is operatively connected to the lever.

11. The system of claim 8, further comprising a release member selectively disengageable from the cradle to permit the cradle to move relative to the base.

12. A biopsy system, comprising:
a biopsy device supported by an adapter, wherein the biopsy device comprises a handpiece and a cutting element having an outer cannula hub removably mounted to the handpiece, wherein the cutting element comprises an outer cannula and an inner cannula disposed within the outer cannula and attached to the handpiece, wherein the outer cannula is connected to the outer cannula hub and defines a tissue receiving opening, wherein the outer cannula hub allows selective removal of the handpiece and inner cannula from the outer cannula; and
wherein the adapter comprises:
a base;
a cradle moveably mounted to the base such that the cradle may move while attached to the base, and wherein the cradle is configured to rotatably support the handpiece therein, the cradle configured to inhibit axial movement of the handpiece relative to the cradle when locked therein; and
an indexing guide moveable with the cradle and including a receptacle within which the outer cannula hub is rotatably received, the indexing guide configured to inhibit rotation and axial movement of the outer cannula hub and outer cannula relative to the indexing guide and the cradle when the outer cannula hub is locked therein, wherein the indexing guide further comprises a pair of legs disposed on either side of a base member, wherein an end portion of each of the legs are attached to the cradle.

13. A biopsy system, comprising:
a biopsy device supported by an adapter, wherein the biopsy device comprises a handpiece and a cutting element having an outer cannula hub, wherein the cutting element comprises an outer cannula connected to the outer cannula hub, the outer cannula defining a tissue receiving opening on a circumferential portion of the outer cannula, an inner cannula disposed within the outer cannula and attached to the handpiece; and
wherein the adapter comprises:
a base; and
a cradle moveably mounted to the base such that the cradle may move while attached to the base, and wherein the cradle is configured to rotatably support the handpiece therein and allowing for rotational positioning of the tissue receiving opening, the cradle configured to inhibit movement of the handpiece relative to the cradle when locked therein.

14. The system of claim 13, further comprising a guide lock, said guide lock configured to inhibit rotation of the tissue receiving opening.

15. The system of claim 13, further including a clamp selectively positionable to stabilize the biopsy device during a medical procedure.

16. The system of claim 13, further including a clamp selectively positionable to allow or inhibit movement of the medical instrument relative to the cradle.

17. The system of claim 16, wherein said clamp engages an outer surface of the biopsy device.

18. A biopsy system, comprising:
a biopsy device supported by an adapter, wherein the biopsy device comprises a handpiece and a cutting element having an outer cannula hub removably mounted to the handpiece, wherein the cutting element comprises an outer cannula and an inner cannula disposed within the outer cannula and attached to the handpiece, wherein the outer cannula is connected to the outer cannula hub and defines a tissue receiving opening, wherein the outer cannula hub allows selective removal of the handpiece and inner cannula from the outer cannula; and
wherein the adapter comprises:
a base;
a cradle moveably mounted to the base such that the cradle may move while attached to the base, and wherein the cradle is configured to rotatably support the handpiece therein, the cradle configured to inhibit axial movement of the handpiece relative to the cradle when locked therein; and
an indexing guide moveable with the cradle and including a receptacle within which the outer cannula hub is rotatably received, the indexing guide configured to inhibit rotation and axial movement of the outer cannula hub and outer cannula relative to the indexing guide and the cradle when the outer cannula hub is locked therein, wherein the indexing guide further comprises at least one channel within which the guide lock is moveably received.

19. The system of claim 18, wherein the guide lock further comprises a slot within which a fastener is disposed.

* * * * *